United States Patent
Freiberg

(10) Patent No.: US 7,112,334 B2
(45) Date of Patent: Sep. 26, 2006

(54) ALLERGY INHIBITION

(76) Inventor: Roberta C. Freiberg, 101 Oldham Pl., Maple Glen, PA (US) 19002

( * ) Notice: Subject to any disclaimer, the term of this patent is extended or adjusted under 35 U.S.C. 154(b) by 589 days.

(21) Appl. No.: 10/106,288

(22) Filed: Mar. 26, 2002

(65) Prior Publication Data

US 2002/0183238 A1 Dec. 5, 2002

Related U.S. Application Data

(60) Provisional application No. 60/295,926, filed on Jun. 5, 2001.

(51) Int. Cl.
*A61K 9/00* (2006.01)
*A61K 6/00* (2006.01)

(52) U.S. Cl. .................. 424/401; 424/400; 424/443; 424/445; 424/446; 514/846

(58) Field of Classification Search ............. 424/400, 424/401, 443, 445, 446; 514/2, 400, 844, 514/846
See application file for complete search history.

(56) References Cited

U.S. PATENT DOCUMENTS

| | | | | |
|---|---|---|---|---|
| 5,538,740 A | * | 7/1996 | Abad | 424/547 |
| 5,562,642 A | * | 10/1996 | Smith et al. | 604/289 |
| 5,716,625 A | * | 2/1998 | Hahn et al. | 424/401 |
| 6,070,384 A | * | 7/2000 | Ra et al. | 424/143.1 |
| 6,090,384 A | * | 7/2000 | Ra et al. | 424/143.1 |
| 6,169,069 B1 | * | 1/2001 | De Lacharriere et al. | 514/2 |
| 6,225,332 B1 | * | 5/2001 | Miller et al. | 514/400 |
| 6,274,626 B1 | * | 8/2001 | Jonasse et al. | 514/568 |
| 2002/0064565 A1 | * | 5/2002 | Karagoezian | 424/661 |
| 2002/0150540 A1 | * | 10/2002 | Yoshikawa et al. | 424/43 |
| 2002/0164775 A1 | * | 11/2002 | Swensen | 435/263 |

* cited by examiner

*Primary Examiner*—S. Tran

(57) ABSTRACT

Allergen contact with a person's allergen-responsive tissues is reduced by removing airborne allergens from body surfaces adjacent the person's eyes. Airborne allergens may be removed from body surfaces adjacent the person's eyes by irrigating such areas with an irrigating fluid or by wiping such areas with a pad. Preferably the irrigating fluid or the pad is treated to augment its effectiveness in removing airborne allergens or otherwise preventing them from entering the eye, and/or to reduce allergy symptoms in the eye area caused by airborne allergens that enter the eye.

17 Claims, No Drawings

ALLERGY INHIBITION

CROSS-REFERENCE TO RELATED APPLICATIONS

Applicant claims the benefit, including the benefit under 35 U.S.C. 119(e)(1), of provisional Patent Application No. 60/295,926 filed Jun. 5, 2001.

BACKGROUND OF THE INVENTION

1. Field of the Invention

This invention relates to methods and apparatus for inhibiting the occurrence of and/or reducing the extent of allergic responses to airborne allergens. More particularly, this invention relates to methods and apparatus for reducing allergen contact with a person's allergen-responsive tissues.

2. Description of Related Art

A significant number of people suffer from allergies. According to some estimates, tens of millions of Americans suffer from allergies to airborne particles such as pollen, animal dander, dust, or mold. One method that people have used to address their allergy problems is oral ingestion of antihistamines. While oral antihistamines can be effective in mitigating allergy symptoms, their use entails exposing the entire body to a pharmaceutical product, and they may produce unpleasant or harmful side effects. Another method that people have used to address their allergy problems is to control their environment in an attempt to reduce their exposure to airborne allergens. For instance, they may try to stay in air-conditioned buildings as much as possible when the air contains a large amount of pollen, or they may try to avoid places where cats or other animals are or have been. This method may be quite inconvenient, and may be of limited effectiveness because it is difficult to avoid at least some contact with airborne allergens.

SUMMARY OF THE INVENTION

In accordance with the present invention, allergen contact with a person's allergen-responsive tissues is reduced by removing airborne allergens from body surfaces adjacent the person's eyes. Airborne allergens may be removed from body surfaces adjacent the person's eyes by irrigating such areas with an irrigating fluid or by wiping such areas with a pad. Preferably the irrigating fluid or the pad is treated to augment its effectiveness in removing airborne allergens or otherwise preventing them from entering the eye, and/or to reduce allergy symptoms in the eye area caused by airborne allergens that enter the eye.

DETAILED DESCRIPTION

Airborne allergens such as pollen, animal dander, dust, and mold typically do not trigger allergic responses when they contact external body surfaces. However, airborne allergens may enter the body via the nose, the mouth, or the eyes and contact allergen-responsive tissues, which may result in an allergic response. As used herein, the term "airborne allergens" means particulate allergens that are typically carried by the air, such as pollen, animal dander, dust, and mold, regardless of whether the particles at any particular time are airborne or reside on some surface; thus "airborne allergens" includes particulate allergens that have been deposited on the skin or other surface of a person after having been airborne. Many allergy symptoms involve the eyes, and the eyes can be an important location of allergen contact with allergen-responsive tissues. Some airborne allergens land directly on the tear film covering the cornea or conjunctiva, where they become entrained in the tear film and may be conveyed into contact with allergen-responsive tissues that the tears contact. Other airborne allergens arrive at the cornea or conjunctiva indirectly; they may first land on adjacent body surfaces such as the eyelashes, eyelids, or eyebrows, and may later become dislodged and contact the cornea or conjunctiva. The latter route to the eye can be significant.

In accordance with the present invention, allergen contact with a person's allergen-responsive tissues is reduced by removing airborne allergens from body surfaces adjacent the eyes. By removing airborne allergens from body surfaces adjacent the eyes, the airborne allergens cannot later become dislodged from such surfaces, enter the eyes, and contact allergen-responsive tissues. Removal of airborne allergens from the eyelids may also effect removal of allergens that have been entrained in the tear film and swept from the cornea or conjunctiva by blinking.

Airborne allergen removal from body surfaces adjacent the eyes may be effected in a variety of ways. Such areas may be irrigated with a fluid. Water or an aqueous solution may be used for this purpose. With an appropriate irrigation fluid, the eye may be irrigated at the same time as are the body surfaces adjacent the eyes. The irrigation fluid may contain components to provide the fluid with particular characteristics or to enhance particular characteristics of the fluid. For instance, substances such as detergents may be included in the irrigation fluid to enhance its ability to remove airborne allergens from the body surfaces adjacent the eyes. Antihistamines may be included in the irrigation fluid to provide topical antihistamine administration to the eyes and/or body surfaces adjacent the eyes. Substances may be included in the irrigation fluid that leave a residue on the body surfaces adjacent the eyes tending to entrain or immobilize airborne allergens that land on such surfaces. Substances may be included in the irrigation fluid that diminish the allergenic effect of airborne allergens that land on such surfaces.

Another way of removing airborne allergens from body surfaces adjacent the eyes is to wipe such surfaces with a pad. Such a pad may be made from paper or cloth, and may be treated so as increase its effectiveness at removing airborne allergens or otherwise inhibit airborne allergens from entering the eye, to reduce the allergenic effect of airborne allergens that land on body surfaces adjacent the eyes, to otherwise alleviate allergy symptoms, or to otherwise improve its characteristics in use. A pad may be treated to render it electrostatically attractive so as to attract and retain airborne allergens; this may be primarily effective for airborne allergens located in the eyelashes and eyebrows, and less effective for airborne allergens located on the eyelids where they may tend to adhere in oils on the skin or in tears or tear residues. A pad may be treated with a fluid to moisten it and enhance its ability to remove airborne allergens from the body surfaces adjacent the eyes. Water or an aqueous solution may be used for this purpose. The pad moistening fluid may contain components to provide the fluid with particular characteristics or to enhance particular characteristics of the fluid. For instance, substances such as detergents may be included in the pad moistening fluid to enhance its ability to remove airborne allergens from the body surfaces adjacent the eyes. Antihistamines may be included in the pad moistening fluid to provide topical antihistamine administration to the eyes and/or body surfaces adjacent the eyes. Substances may be included in the pad moistening fluid that leave a residue on the body surfaces adjacent the eyes tending to entrain or immobilize airborne allergens that land on such surfaces. Substances may be included in the pad moistening fluid that diminish the allergenic effect of airborne allergens that land on such surfaces. Skin-treating substances such as moisturizers may be added to the pad moistening fluid. Pads in accordance with this invention may be individually packaged for convenience in carrying them.

In accordance with the present invention, airborne allergens may be removed from body surfaces adjacent the eyes in a variety of circumstances. Airborne allergens may be removed from body surfaces adjacent the eyes in response to a determination that the person has been exposed to airborne allergens sufficiently to warrant their removal from body surfaces adjacent the eyes. For instance, this determination may be made upon a person experiencing allergy symptoms, or upon determining the amount of airborne allergen that has settled on or about the person, or upon observation that the person has been in an environment where a large exposure to airborne allergens may occur, such as a cat-owner's home or a meadow. Airborne allergens may be removed from body surfaces adjacent a person's eyes in predetermined circumstances, such as periodically or at certain times of day or in connection with predetermined events, such as upon returning home or after travel.

Although particular features and embodiments of the invention have been described herein, variations may no doubt be made by those skilled in the art without departing from the spirit and scope of the invention.

What is claimed is:

1. A method of reducing allergen contact with a person's allergen-responsive tissues comprising the steps of:
    (a) determining that removal of airborne allergens from the person is warranted; and
    (b) removing airborne allergens from external areas of the person's body adjacent the person's eyes.

2. The invention of claim 1, wherein step (a) includes determining that the person is experiencing allergy symptoms.

3. The invention of claim 1, wherein step (a) includes determining that the person has been in an environment where a large exposure to airborne allergens may occur.

4. The invention of claim 1, wherein the determination of step (a) is made in response to the occurrence of predetermined circumstances.

5. The invention of claim 1, wherein step (b) includes irrigating external areas of the person's body adjacent the person's eyes with a fluid.

6. The invention of claim 5, wherein said fluid is an aqueous solution.

7. The invention of claim 5, wherein said fluid includes an antihistamine.

8. The invention of claim 5, wherein said fluid includes a substance leaving a residue on surfaces tending to entrain or immobilize airborne allergens that land on such surfaces.

9. The invention of claim 5, wherein said fluid includes a substance leaving a residue on surfaces tending to diminish the allergenic effect of airborne allergens that land on such surfaces.

10. The invention of claim 1, wherein step (b) includes wiping external areas of the person's body adjacent the person's eyes with a pad.

11. The invention of claim 10, wherein said pad is electrostatically attractive.

12. The invention of claim 10, wherein said pad is moistened with a fluid.

13. The invention of claim 12, wherein said fluid is an aqueous solution.

14. The invention of claim 12, wherein said fluid includes an antihistamine.

15. The invention of claim 12, wherein said fluid includes a substance leaving a residue on surfaces tending to entrain or immobilize airborne allergens that land on such surfaces.

16. The invention of claim 12, wherein said fluid includes a substance leaving a residue on surfaces tending to diminish the allergenic effect of airborne allergens that land on such surfaces.

17. The invention of claim 12, wherein said fluid includes a skin-treating substance.

* * * * *